US008655807B2

(12) United States Patent
Multari et al.

(10) Patent No.: US 8,655,807 B2
(45) Date of Patent: Feb. 18, 2014

(54) METHODS FOR FORMING RECOGNITION ALGORITHMS FOR LASER-INDUCED BREAKDOWN SPECTROSCOPY

(75) Inventors: Rosalie A. Multari, Albuquerque, NM (US); David A. Cremers, Albuquerque, NM (US)

(73) Assignee: Applied Research Associates, Inc., Albuquerque, NM (US)

( * ) Notice: Subject to any disclaimer, the term of this patent is extended or adjusted under 35 U.S.C. 154(b) by 636 days.

(21) Appl. No.: 12/981,626

(22) Filed: Dec. 30, 2010

(65) Prior Publication Data

US 2011/0246145 A1    Oct. 6, 2011

Related U.S. Application Data

(60) Provisional application No. 61/320,992, filed on Apr. 5, 2010.

(51) Int. Cl.
*G06F 1/00* (2006.01)

(52) U.S. Cl.
USPC ............................. 706/12; 702/19; 600/322

(58) Field of Classification Search
USPC .......................................................... 706/12
See application file for complete search history.

(56) References Cited

U.S. PATENT DOCUMENTS

| | | | |
|---|---|---|---|
| 6,639,665 B2 | 10/2003 | Poole | |
| 6,777,241 B1 | 8/2004 | Naumann et al. | |
| 6,985,818 B1 | 1/2006 | Samuels | |
| RE39,672 E | 6/2007 | Shehada et al. | |
| 7,436,510 B2 | 10/2008 | Grun et al. | |
| 7,623,234 B2 | 11/2009 | Puzey | |
| 7,760,354 B2 | 7/2010 | Grun et al. | |
| 7,945,393 B2 | 5/2011 | Treado et al. | |
| 8,082,111 B2 | 12/2011 | Fichet | |
| 2005/0267694 A1 | 12/2005 | Buckley et al. | |
| 2008/0151241 A1* | 6/2008 | Lindfors et al. | 356/318 |
| 2008/0198365 A1 | 8/2008 | Treado | |
| 2009/0012723 A1 | 1/2009 | Treado | |
| 2009/0290151 A1* | 11/2009 | Agrawal et al. | 356/318 |
| 2010/0328661 A1* | 12/2010 | Blais-Ouellette et al. | 356/328 |
| 2011/0237446 A1 | 9/2011 | Treado et al. | |

OTHER PUBLICATIONS

International Search Report and Written Opinion of the International Searching Authority in co-pending case filed under the Patent Cooperation Treaty, International application No. PCT/US2011/028453.

(Continued)

*Primary Examiner* — Kakali Chaki
*Assistant Examiner* — Kalpana Bharadwaj
(74) *Attorney, Agent, or Firm* — Dinsmore & Shohl LLP; Monika J. Hussell, Esq.

(57) ABSTRACT

In one embodiment, a method for forming a recognition algorithm for laser-induced breakdown spectroscopy may include: determining a most mathematically different dataset of a plurality of spectral datasets corresponding to materials; dividing the spectral datasets into model development datasets and performance evaluation datasets; transforming, automatically with a processor, one of the model development datasets into a first discrimination model that discriminates the first spectra; removing the first spectra from the model development datasets to yield a subset of development datasets; determining a next most mathematically different spectral dataset of the spectral datasets; transforming the subset of development datasets into a second discrimination model that discriminates the second spectra; and combining the first discrimination model and the second discrimination model to form the recognition algorithm for laser-induced breakdown spectroscopy.

19 Claims, 4 Drawing Sheets

(56) References Cited

OTHER PUBLICATIONS

Qassem Mohaidat, Sunil Palchaudhuri, and Steven J. Rehse The Effect of Bacterial Environmental and Metabolic Stresses on a Laser-Induced Breakdown Spectroscopy (LIBS) Based Identification of *Escherichia coli* and *Streptococcus viridans* Applied Spectroscopy, vol. 65 Issue 4, pp. 386-392 (2011).
J. J. Remus, J. L. Gottfried, R. S. Harmon, A. Draucker, D. Baron, & R. Yohe Archaeological applications of laser-induced breakdown spectroscopy: an example from the Coso Volcanic Field, California, using advanced statistical signal processing analysis Applied Optics, vol. 49 Issue 13, pp. C120-C131 (2010).
E. Aragon, C. E. McManus, N. J. McMillan, M. Wise, R. S. Harmon, F. De Lucia, and A. Miziolek Provenance of Gem Beryls: Chemometric Analysis by Laser-Induced Breakdown Spectroscopy (LIBS) Coast Section of SEPM Paper No. 156-12, 2008—Joint Mtg of the Geological Soc. of Am, Soil Science Soc of Am, Am. Soc of Agronomy, Crop Science Soc of Am., Gulf Coast Assoc. of Geological Soc. with the Gulf Coast Sect. of SEPM.
N. Labbe, I. M. Swamidoss, N. Andre, M. Z. Martin, T. M. Young and T. G. Rials Extraction of information from laser-induced breakdown spectroscopy spectral data by multivariate analysis Appl. Opt. 47, G158-G165 (2008).
Russell S. Harmon, Frank C. DeLucia, COL Raymond J. Winkel, Jr., Aaron LaPointe, Scott Grossman, Kevin L. McNesby, and Andrzej W. Miziolek LIBS: A New Versatile, Field Deployable, Real-Time Detector System With Potential for Landmine Detection Proceedings of SPIE vol. 5089 (2003) SPIE-0277-786X/03, pp. 1065-1077.
Qianqian Wang, Peter Jander, Cord Fricke-Begemann, Reinhard Noll Comparison of 1064 nm and 266 nm excitation of laser-induced plasmas for several types of plastics and one explosive Spectrochimica Acta Part B 63 (2008) 1011-1015.
Frank C. De Lucia, Jr., Jennifer L. Gottfried, and Andrzej W. Miziolek Evaluation of femtosecond laser-induced breakdown spectroscopy for explosive residue detection Optics Express vol. 17, No. 2 (2009) pp. 419-425.
Caroline McEnnis and James B. Spicer Substrate-Related Effects on Molecular and Atomic Emission in LIBS of Explosives Detection and Sensing of Mines, Explosive Objects, and Obscured Targets XIII, Proc. of SPIE vol. 6953, 695309, (2008)-0277-786X/08 doi: 10.1117/12.782301.
Daniel Mirell, Olivier Chalus, Kristen Peterson, and Jean-Claude Diels Remote sensing of explosives using infrared and ultraviolet filaments J. Opt. Soc. Am. B/vol. 25, No. 7/Jul. 2008, pp. B108-B111.
Susana Cabredoa, Alejandro Parraa, Cecilia Saenza and Jesús Anzanob Bioaerosols chemometric characterization by laser-induced fluorescence: Air sample analysis Talanta vol. 77, Issue 5, Mar. 15, 2009, pp. 1837-1842.
Jennifer L. Gottfried, Frank C. De Lucia, Jr., Chase A. Munson, and Andrzej W. Miziolek Standoff Detection of Chemical and Biological Threats Using Laser-Induced Breakdown Spectroscopy vol. 62, No. 4, 2008 Applied Spectroscopy pp. 353-363.
Diedrich, J; Rehse, S.J; Palchuadhuri, S. Pathogenic *Escherichia coli* strain discrimination using laser-induced breakdown spectroscopy American Institute of Physics, 2007, 102, 014702-1.
Mordmueller, Mario; Bohling, Christian; John, Andreas; Schade, Wolfgang Rapid test for the detection of hazardous microbiological material Proc. SPIE, vol. 7484, 74840F (2009); doi:10.1117/12.830200.
E. Snyder, C. Munson, J. Gottfried, F. De Lucia, Jr., B. Gullett, and A. Miziolek Laser-induced breakdown spectroscopy for the classification of unknown powders Appl. Opt. V. 47, No. 31, G80-G87 (2008).
L. Guyon, M. Baudelet, T. Amodeo, E. Frejafon, P. Laloi, J. Yu and J. P. Wolf Laser-Induced Breakdown Spectroscopy analysis of Bacteria: What Femtosecond Lasers Make Possible Ultrafast Phenomena XV Proceedings of the 15th Int'l Conference, Pacific Grove, USA, Jul. 30-Aug. 4, 2006.
M. Baudelet, L. Guyon, J. Yu, and J.P. Wolf Femtosecond time-resolved laser-induced breakdown spectroscopy for detection and identification of bacteria: A comparison to the nanosecond regime J. of Applied Physics 99, 084701 (2006).
M. Baudelet, J. Yu, M. Bossu, J. Jovelet,J.P. Wolf, T Amodeo, E. Frejafon, and P. Laloi Discrimination of microbiological samples using femtosecond laser-induced breakdown spectroscopy Applied Physics Letters 89 163903 (2006).
Rosemarie Chinni, David A. Cremers, Rosalie Multari Analysis of material collected on swipes using laser-induced breakdown spectroscopy Applied Optics, vol. 49, No. 13, May 1, 2010.
Steven J. Rehse, Qassem I. Mohaidat, and Sunil Palchaudhuri Towards the clinical application of laser-induced breakdown sepctroscopy for rapid pathogen diagnosis: the effect of mixed cultures and sample dilution on bacterial identification Applied Optics, vol. 49, No. 13, May 1, 2010.
J.J. Laserna, L.M. Cabalin, F.J.Fortes LIBS as an advanced tool in the chronocultural study of archaeometallurgical objects http://www.promet.org.gr/Portals/0/ProceedingsPDF/CSSIM-IDT-06.pdf.
S. Duchene, R. Bruder, J.B. Sirven, V. Detalle Chemometrics and Laser Induced Breakdown Spectroscopy (LIBS) Analyses identification of wall painting pigments CMA4CH 2008 March Meeting.
Gottfried Jennifer L., De Lucia Frank C., Munson Chase A., Miziolek Andrzej W Laser-induced breakdown spectroscopy for detection of explosives residues: a review of recent advances, challenges, and future prospects Analytical and Bioanalytical Chemistry ISSN 1618-2642 2009, vol. 395, No. 2, pp. 283-300.
Christopher Brown, Caitlin Rinke, Matthieu Baudelet, Martin Richardson, Michael E. Sigman Substrate Independent Identification of Organic Analytes with LIBS (2009 NASLIBS) http://lpl.creol.ucf.edu/presentations/2009%20-%20NASLIBS%20-%/20Substrate-Independent-Identification-of-Organic-Analytes-with-LIBS_abstract.pdf.
Jennifer L. Gottfried; Frank C. De Lucia Jr.; Chase A. Munson; Christopher Ford; Andrzej W. Miziolek Detection of Energetic Materials and Explosive Residues With Laser-Induced Breakdown Spectroscopy: II. Stand-off Measurements http://www.stormingmedia.us/80/8072/A807274.html (2007).
V. Lazica, A. Paluccia, S. Jovicevicb, C. Poggia and E. Buono Analysis of explosive and other organic residues by laser induced breakdown spectroscopy Spectrochimica Acta Part B: Atomic Spectroscopy vol. 64, Issue 10, Oct. 2009, pp. 1028-1039.
C.G. Brown, M. Baudelet, C. Bridge, M.K. Fisher, M. Sigman, P.J. Dagdigian, M. Richardson Atmosphere Issues in Detection of Explosives and Organic Residues http://lpl.creol.ucf.edu/publications/2009%20-%20SPIE%20Proceedings%20-%20Brown.pdf .
Jennifer L. Gottfried, Frank C. De Lucia, Jr, Chase A. Munson and Andrzej W. Miziolek Strategies for residue explosives detection using laser-induced breakdown spectroscopy J. Anal. At. Spectrom., 2008, 23, 205-216, DOI: 10.1039/b703891g.
F. C. De Lucia, Jr., J. L. Gottfried, C. A. Munson, and A. W. Miziolek Multivariate analysis of standoff laser-induced breakdown spectroscopy spectra for classification of explosive-containing residues Appl. Opt. V. 47, No. 31, G112-G121 (2008).
Andrzej Miziolek, Frank DeLucia, Chase Munson, and Jennifer Gottfrid A new standoff CB detection technology based on the Fusion of LIBS and Raman http://www.chemimage.com/docs/publications/Threat-Detection/CBD%20Summary%20Final%20Rev.pdf.
Doucet, François R.; Belliveau, Thomas F.; Fortier, Jean-Luc; Hubert, Joseph Use of Chemometrics and Laser-Induced Breakdown Spectroscopy for Quantitative Analysis of Major and Minor Elements in Aluminum Alloys Applied Spectroscopy, vol. 61, Issue 3, (Mar. 2007) , pp. 327-332(6).
A. Jurado-López and M. D. Luque de Castro Chemometric Approach to Laser-Induced Breakdown Analysis of Gold Alloys Appl. Spectrosc. V. 57, No. 3, 349-352 (2003).
J. Amador-Hernández, J. M. Fernandez-Romero, M. D. Luque de Castro In-depth characterization of screen-printed electrodes by laser-induced breakdown spectrometry and pattern recognition Surface and Interface Analysis, vol. 31 Issue 4, pp. 313-320 (2001).
M. Kraushaar, R. Noll, and H. U. Schmitz Slag Analysis with Laser-Induced Breakdown Spectrometry Appl. Spectrosc. V. 57, No. 10, 1282-1287 (2003).
Jean-Baptiste Sirven, Agnès Pailloux, Yacine M'Baye, Nadine Coulon, Thierry Alpettaz and Stéphane Gossé Towards the determi-

(56) References Cited

OTHER PUBLICATIONS nation of the geographical origin of yellow cake samples by laser-induced breakdown spectroscopy and chemometrics J. Anal. At. Spectrum., 2009, 24, 451-459, DOI: 10.1039/b821405k.

Jean-Baptiste Sirven, Beatrice Salle, Patrick Mauchien, Jean-Luc Lacour, Sylvestre Maurice, and Girard Manhes Feasibility study of rock identification at the surface of Mars by remote laser-induced breakdown spectroscopy and three chemometric methods J. Anal. At. Spectrom., 2007, vol. 22, No. 12, 1471-1480.

Gottfried, Jennifer, Harmon, Russell , De Lucia, Frank C. Jr, and Miziolek, Andrzej W. Multivariate analysis of laser induced breakdown spectroscopy chemical signatures for geomaterial classification Spectrochemica Acta Part B 64 (2009) 1009-1019.

Philip J. Brown, Clifford H. Spiegelman, Michael C. Denham Chemometrics and Spectral Frequency Selection Philosophical Transactions of the Royal Society of London Series A—Physical Sciences and Engineering, Dec. 16, 1991; v.337, No. 1647, p. 311-322.

J. Yun, R. Klenze, and J. Kim Laser-Induced Breakdown Spectroscopy for the On-Line Multielement Analysis of Highly Radioactive Glass Melt Simulants. Part II: Analyses of Molten Glass Samples Appl. Spectrosc. V. 56, No. 7, 852-858 (2002).

C. Bohling, K. Hohmann, D. Scheel, W. Schade, M. Reuter, and G. Holl Anti-Personnel-Mine Detection by Laser-Induced Breakdown Spectroscopy Conference on Lasers and Electro-Optics/Quantum Electronics and Laser Science and Photonic Applications, Systems and Technologies, Technical Digest (CD) (Optical Society of America, 2005), paper PWD3.

C. Bohling, D. Scheel, K. Hohmann, W. Schade, M. Reuter, and G. Holl Fiber-optic laser sensor for mine detection and verification Appl. Opt. 45, No. 16, 3817-3825 (2006).

M. Z. Martin, N. Labbé, N. André, R. Harris, M. Ebinger, S. D. Wullschleger, and A. A. Vass High resolution applications of laser-induced breakdown spectroscopy for environmental and forensic applications Spectrochimica Acta Part B: Atomic Spectroscopy, vol. 62, Issue 12, Dec. 2007, pp. 1426-1432.

F. Doucet, M. Tourigny, M. Sabsabi, R. Lyon, P.Faustino Enabling Molecular Analysis with laser induced Breakdown Spectroscopy using Chemometrics web-application to pharmaceuticals.

François R. Doucet, Patrick J. Faustino, Mohamad Sabsabi and Robbe C. Lyon Quantitative molecular analysis with molecular bands emission using laser-induced breakdown spectroscopy and chemometrics J. Anal. At. Spectrom., 2008, vol. 23, 694 -701, DOI: 10.1039/b714219f.

Márcio José Coelho Pontesa, Juliana Cortezb, Roberto Kawakami Harrop Galväoc, Celio Pasquinib, Mário César Ugulino Araújoa, Ricardo Marques Coelhod, Márcio Koiti Chibad, Mônica Ferreira de Abreud and Beáta Emöke Madarie Classification of Brazilian soils by using LIBS and variable selection in the wavelet domain Analytica Chimica Acta, vol. 642, 2009, pp. 12-18.

Michael E. Essington, Galina V. Melnichenko, Melanie A. Stewart and Robert A. Hull Soil Metals Analysis Using Laser-Induced Breakdown Spectroscopy (LIBS) Soil Sci Soc Am J 73:1469-1478 (2009).

J.B. Sirven, B. Bousquet, L.Canioni, and L. Sarger Laser-Induced breakdown spectroscopy Composite Samples: Comparison of Advanced Chemometric Methods Anal. Chem. 2006, vol. 78, No. 5, 1462-1469.

E. Ferreira, J. Anzano, D. Milori, E. Ferreira, R. Lasheras, B. Bonilla, B. Montull-Ibor, J. Casas, and L. Neto Multiple Response Optimization of Laser-Induced Breakdown Spectroscopy Parameters for Multi-element Analysis of Soil Samples Appl. Spectrosc. vol. 63, No. 9, 1081-1088 (2009).

B. Bousquet, J.-B. Dirven, L. Canioni Towards quantitative laser-induced breakdown spectroscopy analysis of soil samples Spectrochimica Acta Part B 62 (2007) 1582-1589.

Jennifer L. Gottfried Discrimination of biological and chemical threat simulants in residue mixtures on multiple substrates Anal Bioanal Chem Published on line Feb. 18, 2011 DOI 10.1007/s00216-011-4746-4.

Francois R. Doucet, Gregg Lithgow, Rick Kosierb, Paul Bouchard and Mohamad Sabsabi Determination of isotope ratios using Laser-Induced Breakdown Spectroscopy in ambient air at atmospheric pressure for nuclear forensics JAAS Dynamic Article DOI: 10.1039/c0ja00199f Dec. 2010.

Vincent Motto-Ros, Alexander S. Koujelev, Gordon R. Osinski, Alexander E. Dudelzak Quantitative multi-elemental laser-induced breakdown spectroscopy using artificial neural networks Journal of the European Optical Society ISSN 1990-2573 rapid publications 08011 (2008).

J. B. Sirven, B. Bousquet, L. Canioni, L. Sarger, S. Tellier, M. Potin-Gautier, I. Le Hecho Qualitative and quantitative investigation of chromium-polluted soils by laser-induced breakdown spectroscopy combined with neural networks analysis Anal Bioanal Chem (2006) 385: 256-262 DOI 10.1007/s00216-006-0322-8.

R. Sattmann, I. Monch, H. Krause, R. Noll, S. Couris, A. Hatziapostolou, A. Mavromanolakis, C. Fotakis, E. Larrauri, and R. Miguel Laser-Induced Breakdown Spectroscopy for Polymer Identification Appliedspectroscopy, vol. 52, No. 3, p. 456—(1998).

A. Koujelev, M. Sabsabi, V. Motto-Ros, S. Laville, S. L. Lui Laser induced breakdown spectroscopy with artificial neural network processing for material identification Planetary & Space Science doi:10.1016/j.pss.2009.06.022.

Christian Bohling, Konrad Hohmann, Dirk Scheel, Christoph Bauer, Wolfgang Schippers, Jörg Burgmeier, Ulrike Willer, Gerhard Roll, Wolfgang Schade All-fiber-coupled laser-induced breakdown spectroscopy sensor for hazardous materials analysis Spectrochimica Acta Part B 62 (2007) 1519-1527.

Alexander A. Bol'Shakov, Jong H. Yoo, Chunyi Liu, John R. Plumer, and Richard E. Russo Laser-induced breakdown spectroscopy in industrial and security applications Applied Optics / vol. 49, No. 13 / May 1, 2010.

Jaime A. Stearns, Sarah E. McElman, and James A. Dodd Identification of vapor-phase chemical warfare agent stimulant and rocket fuels using laser-induced breakdown spectroscopy May 1, 2010 / vol. 49, No. 13 / Applied Optics.

Steven J. Rehse Laser-Based Identification of Pathogenic Bacteria The Physics Teacher ♦ vol. 47, Mar. 2009.

Steven J. Rehse, Qassem Mohaidat, Sunil Palchaudhuri Laser-Induced Breakdown Spectroscopy (LIBS) for the Rapid Field Identification and Classification of Pathogenic Bacteria OSA / ASSP/ LACSEA/LS&C 2010.

\* cited by examiner

METHODS FOR FORMING RECOGNITION ALGORITHMS FOR LASER-INDUCED BREAKDOWN SPECTROSCOPY

CROSS-REFERENCE TO RELATED APPLICATIONS

This application claims the benefit of U.S. Provisional Application No. 61/320,992, filed Apr. 5, 2010 entitled "METHODS OF DEVELOPING A DATA ANALYSIS ALGORITHM FOR THE DISCRIMINATION OF MATERIALS SUCH AS METALS, CHEMICAL SUBSTANCES, PATHOGENS, AND EXPLOSIVES VIA LASER-INDUCED BREAKDOWN SPECTROSCOPY IN COMBINATION WITH CHEMOMETRIC DATA ANALYSIS."

TECHNICAL FIELD

The present specification generally relates to methods for forming recognition algorithms and, more specifically, methods for forming recognition algorithms for identifying materials with laser-induced breakdown spectroscopy (LIBS).

BACKGROUND

LIBS is a spectroscopic analysis technique in which a laser pulse vaporizes ng to μg quantities of material and thermally excites the vaporized material in a short-lived plasma (~8000 K). Light emitted from atoms, ions, and simple molecules in the plasma is collected and analyzed. LIBS may be utilized for elemental analysis to determine the composition of the target material via unique element fingerprint spectra, i.e., by observing specific spectral emission lines characteristic of light emitted from a sample that correspond to particular elements.

LIBS may be extended from identification of individual elements to identification of materials such as metals, chemical substances, pathogens, and explosives. In these cases, the shape of the LIBS spectral data may be used for identification of materials as opposed to particular elemental lines. The spectral data generally include multiple elemental and background emissions over an observed range of wavelengths. The spectral data may be collected from a LIBS instrument and input to an algorithm for identification. However, such algorithms are difficult to develop because the algorithms must differentiate relatively complex spectral data, which may include data derived information pulled from the spectra.

Accordingly, a need exists for alternative methods for forming recognition algorithms for identifying materials with LIBS.

SUMMARY

In one embodiment, a method for forming a recognition algorithm for laser-induced breakdown spectroscopy may include: determining a most mathematically different dataset of a plurality of spectral datasets corresponding to materials; dividing the spectral datasets into model development datasets and performance evaluation datasets; transforming, automatically with a processor, one of the model development datasets into a first discrimination model that discriminates the first spectra; removing the first spectra from the model development datasets to yield a subset of development datasets; determining a next most mathematically different spectral dataset of the spectral datasets; transforming the subset of development datasets into a second discrimination model that discriminates the second spectra; and combining the first discrimination model and the second discrimination model to form the recognition algorithm for laser-induced breakdown spectroscopy. The most mathematically different dataset may include first spectra indicative of light emitted from a first vaporized material. The model development datasets and the performance evaluation datasets may include the first spectra. The next most mathematically different spectral dataset may include second spectra indicative of light emitted from a second vaporized material.

In another embodiment, a method for forming a recognition algorithm for laser-induced breakdown spectroscopy may include: collecting spectral datasets corresponding to materials with a laser-induced breakdown spectroscopy instrument; dividing the spectral datasets into model development datasets and performance evaluation datasets; transforming, automatically with a processor, the model development datasets into an overall discrimination model; ranking the spectral datasets from most mathematically different to least mathematically different according to the overall discrimination model; creating an individual discrimination model to discriminate a most mathematically different spectral dataset; and forming the recognition algorithm for laser-induced breakdown spectroscopy. Each of the spectral datasets may include spectra indicative of light emitted from one of the materials. The overall discrimination model may identify each of the materials. The recognition algorithm may include the individual discrimination model.

In yet another embodiment, a method for forming a recognition algorithm for laser-induced breakdown spectroscopy may include: collecting spectral datasets corresponding to materials with a laser-induced breakdown spectroscopy instrument; transforming, automatically with a processor, the spectral datasets into individual discrimination models; and forming the recognition algorithm for laser-induced breakdown spectroscopy. Each of the spectral datasets may include spectra indicative of light emitted from one of the materials. Each of the individual discrimination models may discriminate one of the spectral datasets. The recognition algorithm may include the individual discrimination models ordered from highest discrimination capability to lowest discrimination capability. The recognition algorithm may invoke the individual discrimination models in order.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

The embodiments described herein generally relate to methods for forming algorithms for identifying materials with laser-induced breakdown spectroscopy (hereinafter LIBS). Generally, recognition algorithms are formed by inputting spectral datasets into a processor executing machine readable instructions and transforming the input into a recognition algorithm. Various embodiments of methods for forming recognition algorithms will be described in more detail herein.

Figure 1:
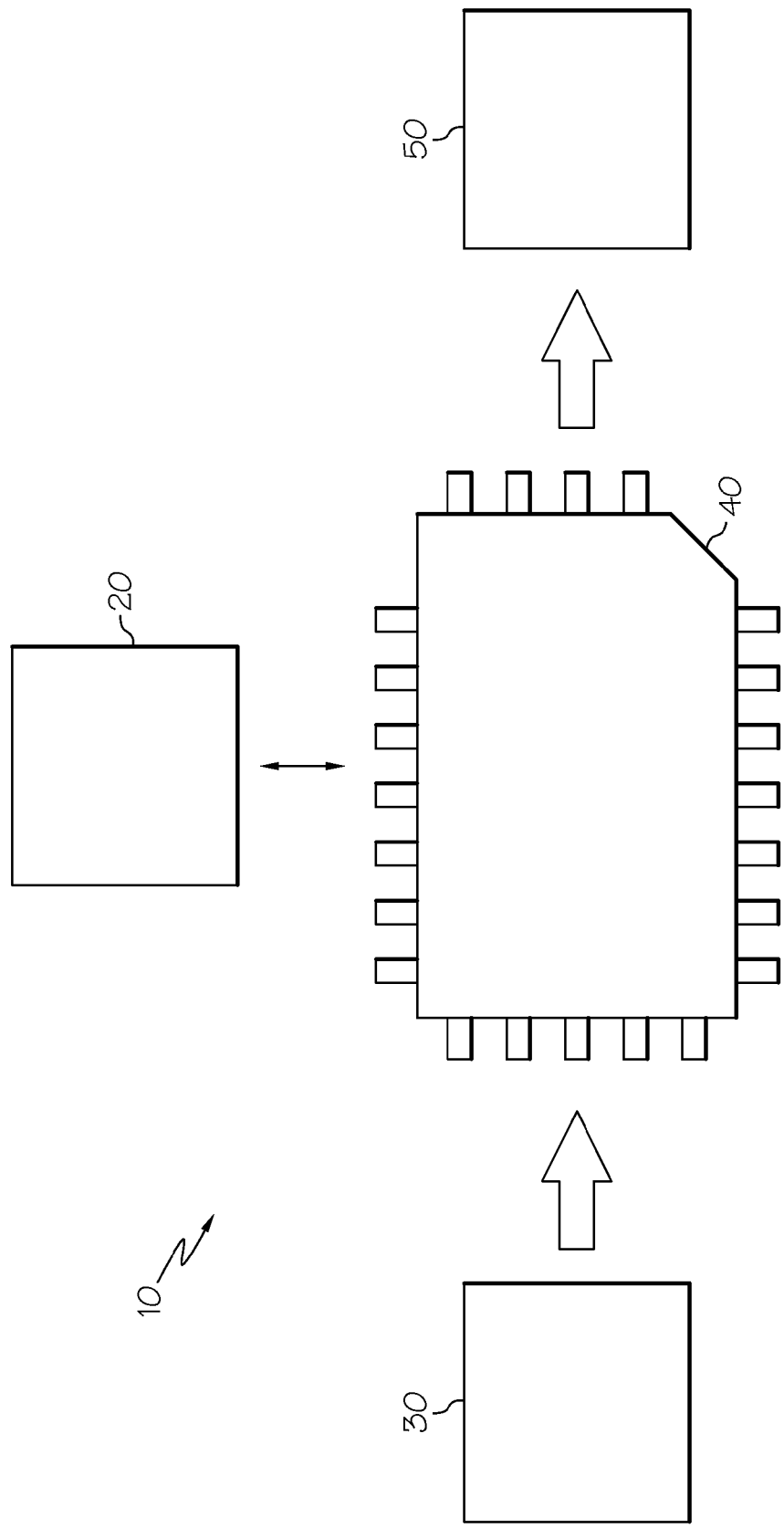
FIG. 1 schematically depicts a method for forming a recognition algorithm according to one or more embodiments shown and described herein.

Referring now to FIG. 1, an embodiment of a method 10 for forming recognition algorithms for identifying materials with LIBS is schematically depicted. The method comprises the step 30 of inputting spectral data into a processor 40 executing machine readable instructions 20 and outputting results for analysis and the step 50 of taking the analysis results and transforming them into the recognition algorithm.

The step 30 of inputting spectral data into a processor 40 executing machine readable instructions 20 may include receiving spectral data or collecting the spectral data. A sufficient number of individual spectra (e.g., one hundred) can be collected for each material (alone or in a single matrix) to capture the variability in spectral data characteristic of the LIBS instrument 100. The collected spectra are transmitted (during the capture or collection processes, or thereafter) to and stored on one or more machine readable mediums or other device(s) capable of storing spectral data, as hereinafter described. Thus, the spectral data may be input to the processor 40 from any type of external device or communication interface to the processor 40 or the spectral data may be generated by the processor 40, e.g., calculated from measured parameters. As used herein, the term "processor" means an integrated circuit, a microchip, a computer, or any other computing device capable of executing the machine readable instructions 20. Although not depicted in FIG. 1, the processor 40 may be communicably coupled to a machine readable medium for storing electronic data. The machine readable medium may be RAM, ROM, a flash memory, a hard drive, or any device capable of storing machine readable instructions. Thus, any input or output of the processor 40 may be stored on the machine readable medium.

Furthermore, it is noted that the phrases "machine readable instructions," "algorithm," and "software" denote logic written in any programming language of any generation (e.g., 1GL, 2GL, 3GL, 4GL, or 5GL) such as, for example, machine language that may be directly executed by the processor, or assembly language, object-oriented programming (OOP), scripting languages, microcode, etc., that may be compiled or assembled and stored on a machine readable medium. Alternatively, the logic may be written in a hardware description language (HDL), such as implemented via either a field-programmable gate array (FPGA) configuration or an application-specific integrated circuit (ASIC), and their equivalents.

Figure 2:
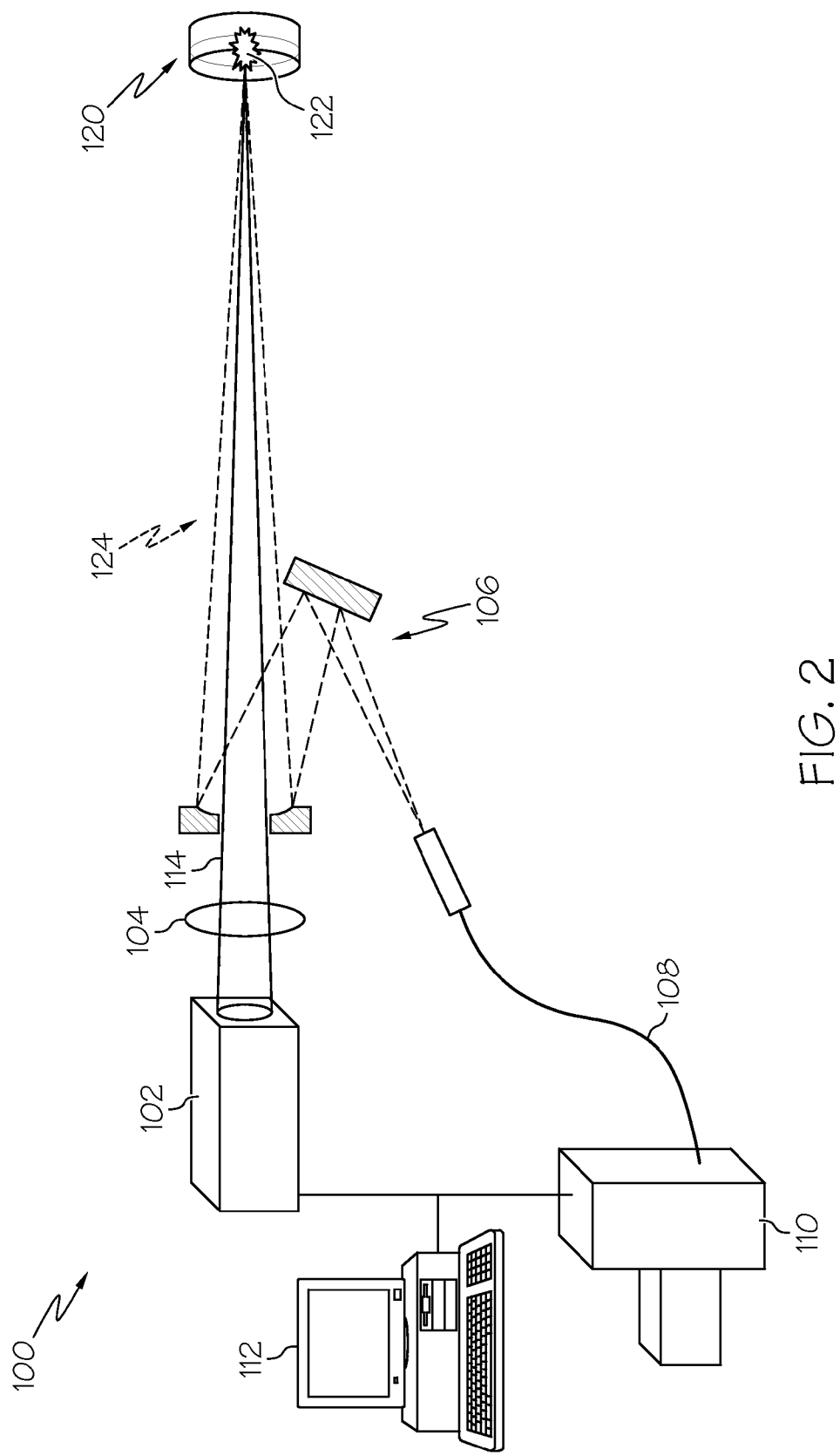
FIG. 2 schematically depicts a laser-induced breakdown spectroscopy instrument according to one or more embodiments shown and described herein.

Referring now to FIG. 2, it is noted that the spectral data may be collected with a LIBS instrument 100. In FIG. 2, one embodiment of the LIBS instrument 100 for collecting spectral data is schematically depicted. The LIBS instrument 100 comprises a laser 102 for vaporizing a material 120 to generate a plasma 122 and a sensor 110 for transforming a light 124 emitted from the plasma 122 into electronic data. In the depicted embodiment the laser 102 and the sensor 110 are communicatively coupled to a processor 112 to coordinate the collection of spectral data.

For example, spectral data may be collected by synchronizing the emission of a laser light 114 from the laser 102 and collecting light 124 emitted by the plasma 122. In the embodiment depicted in FIG. 2, laser light 114 is generated by the laser 102 and transmitted though a focusing lens 104 to focus it onto the material 120 and generate the plasma 122. It is noted that the term "light" as used herein refers to various wavelengths of the electromagnetic spectrum, particularly wavelengths from about 100 nm to about 1200 nm such as, for example, from about 200 nm to about 1000 nm.

In the depicted embodiment, a light 124 is emitted from the plasma 122 through the reflection system 106, which, as depicted in FIG. 2, may comprise two mirrors, to a light guide 108 (depicted in FIG. 2 as a fiber optic). The light guide 108 may include any material that transmits light such as, but not limited to, a cylindrically shaped glass or polymer material that transmits light along its axis. The light 124 is transmitted to the sensor 110 which is capable of transforming the light 124 into spectral data. For example, the sensor 110 may include a spectrometer such as, for example, an echelle spectrometer or a polychromator. The sensor 110 may then transmit the spectral data to the processor 112. It is noted that, while a particular embodiment of the LIBS instrument is described above, the LIBS instrument may be any device capable of transforming laser induced plasma light into electronic data indicative of the spectral components of light generated by the plasma.

Figure 3:
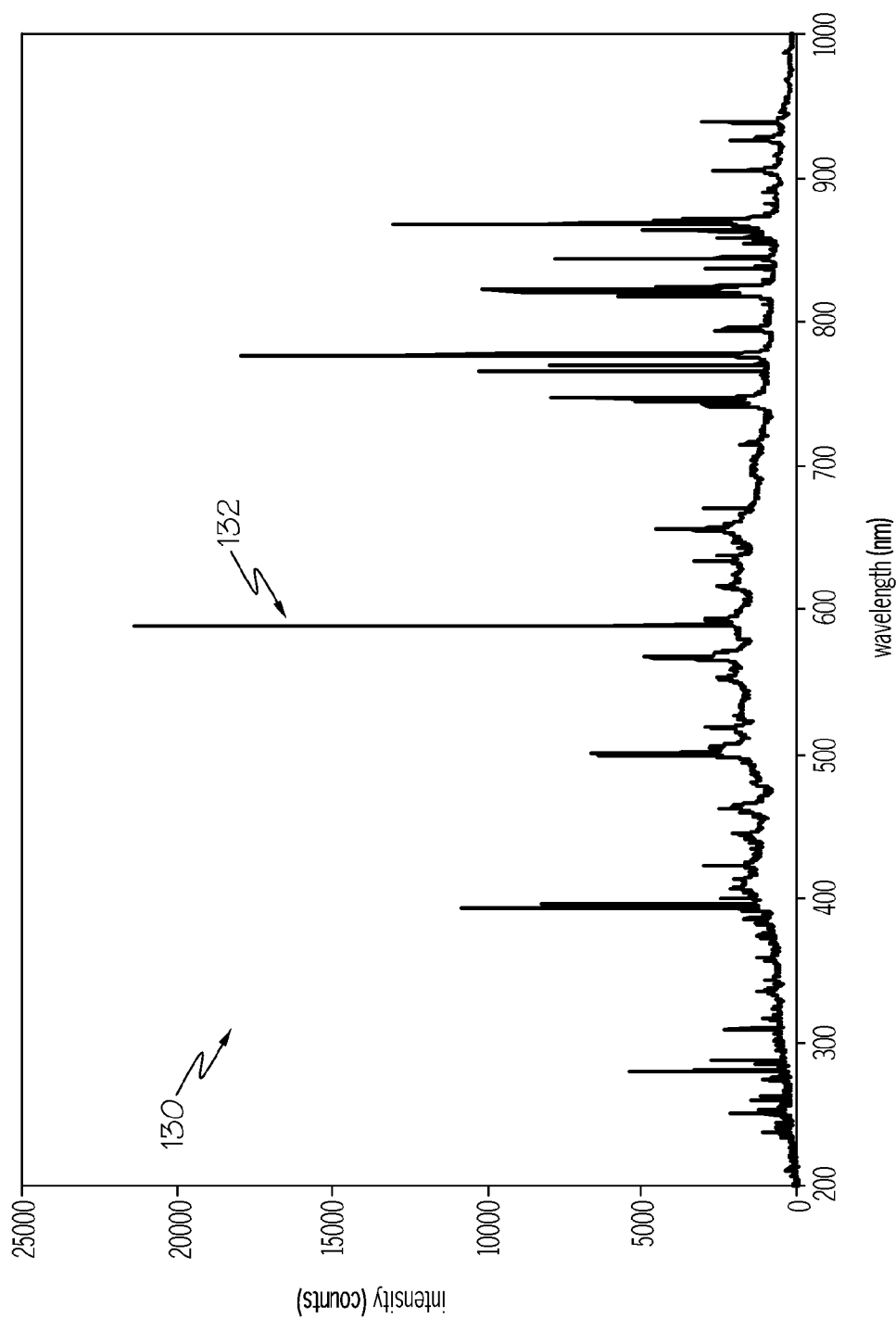
FIG. 3 schematically depicts a spectrum generated by a laser-induced breakdown spectroscopy instrument according to one or more embodiments shown and described herein.

Referring collectively to FIGS. 2 and 3, an embodiment of a spectrum 130 is graphically depicted with wavelength (nm) on the axis of abscissa and intensity (counts) on the axis of ordinates. The spectrum 130 is indicative of the magnitude of the intensity of the light 124 at a specific wavelength emitted from the plasma 122 generated from the material 120. The spectrum 130 comprises elemental lines 132 (i.e., local maxima) and background emissions. While not intending to be bound to any theory, the elemental lines 132 generally correspond to emissions from individual elements such as carbon, nitrogen, oxygen, hydrogen and the like and each spectrum 130 may be indicative of and correspond to a specific material (i.e., plasma generated from soil). Each spectrum may be an individual data sample detected by a LIBS instrument 100, an accumulation of multiple data samples detected by a LIBS instrument 100, or an average of multiple data samples detected by a LIBS instrument 100. For example, in one embodiment, each spectrum represents an accumulation (e.g., summation, or other known data combination technique) of ten data samples collected by the sensor 110 (e.g., sensor acquisition parameters: 1 μs delay, 20 μs window and an exposure period of 1 s).

The LIBS instrument 100 described above may be utilized to collect spectra 130 from materials such as, for example, metals, chemical substances, pathogens, or explosives of interest, either as a pure material or combined in a matrix of other materials (non-limiting examples including Tributyl Phosphate (TBP) on aluminum, Trinitrotoluene on wood, *Escherichia coli* on broccoli). Thus, the embodiments described herein may be utilized for both sample identification and trace element detection in aerosols, liquids, and solids, detection of explosives, compositional analysis of rocks and soils, and sorting of metals.

Figure 4:
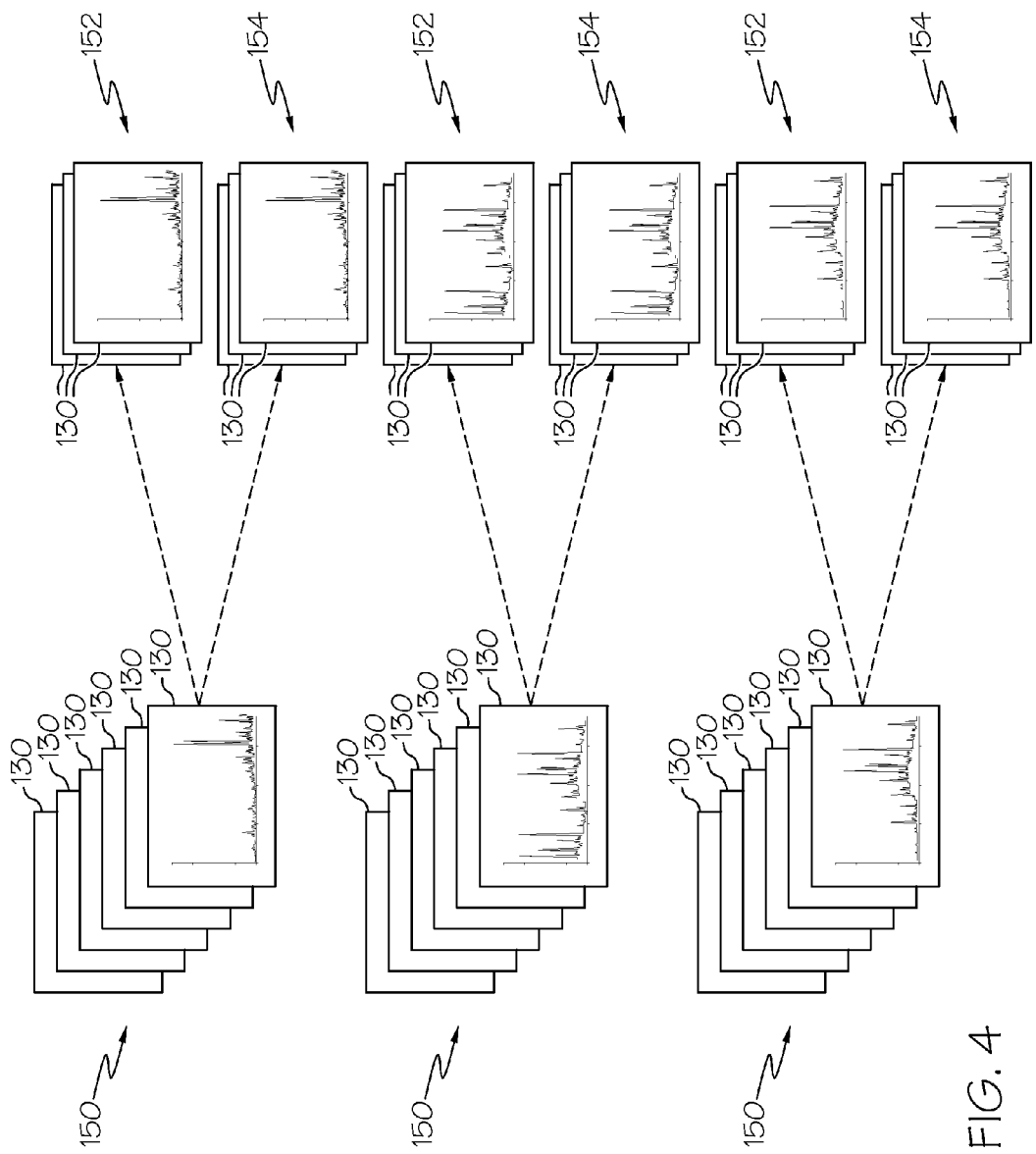
FIG. 4 depicts spectral datasets according to one or more embodiments shown and described herein.

Referring collectively FIGS. 1 and 4, the machine readable instructions 20 may include logic for processing the spectral data input into the processor 40. In one embodiment, the spectra 130 of the spectral datasets 150 are divided into model development datasets 152 for model development and performance evaluation datasets 154 for model performance verification. Each of the spectral datasets 150 comprises spectra 130 collected from a single material or material types. For example, if a recognition algorithm were being developed to identify two materials one of the spectral datasets 150 would comprise spectra 130 collected from a first material and another one of the spectral datasets 150 would comprise spectra 130 collected from a second material. The spectra may be collected from a single sample of the material (e.g., a single piece of metal) or multiple samples of a type of material (e.g., multiple pieces of a single type of metal).

It is noted that the spectral datasets 150 may be divided such that representative spectral measurements are divided into two datasets using a number of methods. One of the datasets may be used for model development and one of the datasets may be used for model performance evaluation. Specifically, the spectral datasets 150 may be divided such that the model development datasets 152 and the performance evaluation datasets 154 each comprise substantially balanced intensity measurements (e.g., representative intensity measurements) according to the intensity maxima of the spectra 130 or area under the intensity curve of the spectra 130. For example, the spectra 130 may be divided such that the sum of the intensity measurements of the spectra in the model development dataset 152 is substantially equal to the sum of the intensity measurements of a corresponding (i.e., indicative of the same material) performance evaluation dataset 154. In another embodiment, the spectral datasets 150 may be divided such that both the model development datasets 152 and performance evaluation datasets 154 comprise spectra 130 with similarly distributed maximum intensities. In a further embodiment, the spectral datasets 150 may be divided such that the model development datasets 152 comprise the spectra 130 with the highest intensity measurements and the performance evaluation datasets 154 comprise the corresponding spectra 130 with the lowest intensity measurements. The overall intensity may be determined based on the area under the intensity curve for each of the spectra 130 or any other method that quantifies the relative magnitude of the intensity curve. For example, a spectral dataset 150 having one hundred spectra 130 can be divided into a model development dataset 152 having the fifty spectra 130 with the highest maximum intensities and a performance evaluation dataset 154 having the fifty spectra with the lowest maximum intensities, and vice versa.

While the spectral datasets 150, the model development datasets 152 and the performance evaluation datasets 154 are depicted in FIG. 4 as having even numbers of spectra 130, it is noted that they may have an even or odd number of spectra 130. Furthermore, all of the spectra 130 within spectral datasets 150 may or may not be included in the model development datasets 152 and the performance evaluation datasets 154. Thus, the model development datasets 152 and the performance evaluation datasets 154 may have equal or unequal numbers of spectra 130. For example, a spectral dataset 150 having one hundred spectra 130 can be divided into a model development dataset 152 having fifty spectra 130 and a performance evaluation dataset 154 having fifty spectra, a model development dataset 152 having seventy spectra 130 and a performance evaluation dataset 154 having thirty spectra 130 or a model development dataset 152 having fifty-nine spectra 130 and a performance evaluation dataset 154 having twenty-three spectra 130 (i.e., excluding eighteen spectra).

Spectra 130 may be excluded from inclusion in the model development datasets 152 and the performance evaluation datasets 154 to balance the intensities or to exclude undesired data. In one embodiment, the spectra 130 in the spectral datasets 150, the model development datasets 152 and the performance evaluation datasets 154 are screened for abnormal or uncharacteristic spectra. The abnormal or uncharacteristic spectra can be removed from the spectral datasets 150, the model development datasets 152 or the performance evaluation datasets 154. Screening may be based on heuristic methods, known errors or evaluations using statistics such as, for example, standard deviation, analysis of variance and the like.

In the embodiments described herein, spectral normalization may be applied to the spectra 130. Non-limiting examples of this normalization include multiplying the spectrum 130 by a value such that the area underneath the spectrum 130 is equal to one or the maximum intensity of the spectrum 130 is equal to one.

In one embodiment, a chemometric analysis or other mathematically based differentiation analysis (such as neural network analysis) is performed to determine the most different dataset of the spectral datasets 150 for the analysis method applied. The differentiation analysis may be performed heuristically or with a model (e.g., utilizing chemometric analysis software) to determine the spectral data set that is easiest to discriminate from the other spectral datasets 150 for the analysis method chosen. For example, an overall discrimination model may be built to analyze all of the spectra 130 at once. After building the overall discrimination model, the performance evaluation datasets 154 may be evaluated using the overall discrimination model results to rank the spectral datasets according to analysis distinctness. The most separated spectral dataset as determined by the overall discrimination model is the most analytically different spectral dataset. Thus, the spectral datasets 150 may be ranked from the easiest to discriminate to hardest to discriminate according to the overall discrimination model results. Alternatively, the spectral datasets 150 may be ranked heuristically.

It is noted that as used herein the phrase "discrimination model" refers to machine readable instructions capable of being executed to differentiate or identify an input spectrum generated by a material. The discrimination models may comprise at least one of: a discriminative functional analysis, both linear correlation and partial least squares regression discriminative analysis, multiple linear regression, neural network analysis, principal component analysis, canonical correlation, redundancy analysis, multiple regression analysis, multivariate analysis of variance, and single or multivariable principal component analysis with multivariate regression. In the embodiments described herein discrimination models may be generated by software executed by a processor (e.g., Unscrambler by Camo Software Inc. of Woodbridge, N.J. USA, Matlab by Mathworks of Natick, Mass., U.S.A., and any other software capable of chosen discriminative analysis). Furthermore, it is noted that discrimination models may be developed to recognize specific materials (e.g., copper), classes of materials (e.g., metals) or heuristically grouped materials (copper and materials who spectra share similar characteristics with the spectra of copper) according to their spectra. Thus, any individual discrimination model may be developed to differentiate a single material or multiple materials based on observed spectra.

Referring collectively to FIGS. 1 and 4, the method 10 comprises the step 50 of transforming the input into the recognition algorithm. The spectral datasets 150 are used to create individual discrimination models which, when combined, are capable of identifying a sample according to its LIBS spectrum 130. For example, a first discrimination model may be built from a first model development dataset. The performance of the first discrimination model may then be evaluated using a first performance evaluation dataset that corresponds to the first model development dataset (i.e., divided from the same spectral dataset or corresponding to the same material). Once adequate discrimination performance is achieved for the first discrimination model, the first model development dataset is removed from the modeling development datasets to yield a subset of development datasets. If sufficient model development datasets remain in the subset of development datasets, a second discrimination model may be built from a second model development dataset. The performance of the second discrimination model may then be evaluated using a second performance evaluation dataset that corresponds to the second model development dataset (i.e., divided from the same spectral dataset or corresponding to the same material). Once adequate discrimination performance is achieved for the second discrimination model, the second model development dataset may be removed from the subset of development datasets. Assuming sufficient spectra remain in the subset of development datasets, a third discrimination model may be built from a third model development dataset, as described herein.

In the embodiments described herein, individual discrimination models can be built according to the process of model building, discrimination, and elimination described above. As the process is iterated, a next spectral dataset may be transformed into a next model that discriminates the next spectral dataset from the spectra in the subset of development datasets. Then the next spectral dataset may be removed from the subset of development datasets. The process may be repeated until the subset of development datasets comprises only one of the spectral datasets. Generally, the process is repeated until all the model development datasets 152 of interest have been discriminated down to an individual model development dataset 152 (i.e., a group of spectra 130 and/or an individual spectrum 130). The individual discrimination model(s) is (are) then tested on the performance evaluation datasets 154, and refined as needed until adequate identification performance is achieved for each of the individual discrimination model(s) (i.e., the individual discrimination model identifies the desired material with sufficient accuracy).

In one embodiment, the individual discrimination models are built in order of the most mathematically different to least mathematically different. For example, the overall discrimination model can be utilized to rank the spectral datasets from most mathematically different to least mathematically different. The process of model building, discrimination, and elimination may then operate according to the ranking of spectral datasets. That is, the individual discrimination model corresponding to the most mathematically different spectral dataset may be built first and the most mathematically different spectral dataset may be removed first. The individual discrimination model corresponding to the next most mathematically different spectral dataset may be built second and the next most mathematically different spectral dataset may be removed second, and so on.

In the embodiments described herein, the recognition algorithm is created by combining the individual discrimination models such that the individual discrimination models are invoked in series and/or in parallel to one another. In the embodiments where the individual discrimination models are invoked in series, a test spectrum is input into the recognition algorithm and each of the individual models is invoked sequentially. For example, but without limiting the foregoing, a first individual discrimination model may be invoked to differentiate the test spectrum among certain possible material choices, and a second individual discrimination model may further differentiate the test spectrum among other possible material choices. In the embodiments where the individual discrimination models are invoked in parallel, the test spectrum is input into the recognition algorithm and multiple individual discrimination models may be invoked simultaneously.

Thus, the recognition algorithm comprises the individual discrimination models arranged according to a model test flow. The model test flow specifies the invocation of individual discrimination models and may be defined subsequent to the creation of the individual discrimination models. In one embodiment, the individual discrimination models are evaluated using the performance evaluation datasets 154 (FIG. 4). For example, the discrimination capability of each individual discrimination model may be evaluated and ranked according to accuracy, i.e., the probability that each of the individual discrimination models correctly identifies the material associated with the spectra in the performance evaluation datasets 154. The ranking may then be utilized to define the model test flow. Specifically, the individual discrimination models may be applied sequentially as needed to differentiate all materials included in the algorithm development. Alternatively, similarly ranked discrimination models may be applied in parallel or the individual discrimination models may be arranged in order with an alternative model test flow. Furthermore, it is contemplated that the discrimination capability may also be assessed through testing or deployment in the field (i.e., accuracy and robustness may be observed). Therefore, the individual discrimination models may be applied from highest discrimination capability to lowest discrimination capability.

In another embodiment, the model test flow may be defined such that the individual discrimination models of the recognition algorithm are ordered from most mathematically different to least mathematically different as determined by the overall discrimination model, described hereinabove. Thus, the model test flow may be based upon the spectral datasets corresponding to the individual discrimination models.

According to the embodiments described herein, the model test flow may be further refined after the recognition algorithm is defined. Known spectra such as the performance evaluation datasets 154 may utilized to analyze the performance of the recognition algorithm. In one embodiment, the performance evaluation datasets 154 are normalized and analyzed by the recognition algorithm. The accuracy of the recognition algorithm may then be assessed based on correctly matching the spectra to their associated materials. The performance of the recognition algorithm as a whole or its constituent individual discrimination algorithms may then be utilized to develop screening parameters. For example, the screening parameter may be a statistic (e.g., average, standard deviation, etc.) that is incorporated into the model test flow to improve the accuracy of the recognition algorithm (i.e., a formula using the standard deviation associated with the discrimination model prediction results may be created and the decision of whether or not to identify the input spectra as indicated by the discrimination model results may be made based on the formula results). After the recognition algorithm is modified by incorporating screening parameters, the known spectra may again be evaluated by the recognition algorithm to reevaluate discrimination performance. For the testing of unknown spectra using the recognition algorithm in practice, screening parameters may be used in combination with prediction results to determine if spectral data of the sample are valid for discrimination using the recognition algorithm.

Once the recognition algorithm is constructed, the recognition algorithm may be incorporated into a LIBS instrument such as, for example, the LIBS instrument that collected the spectral datasets 150. Specifically, with reference to FIG. 2, the recognition algorithm may cooperate with the control system of the LIBS instrument 100 (e.g., LabVIEW 8.6 by National Instruments of Austin, Tex. U.S.A.). As such the recognition algorithm may be executed by the processor 112 for automated, real-time analysis of LIBS spectra input directly from the output of sensor 110. From the user operational perspective, the LIBS instrument 100 may configured such that a single button is "clicked" to: send a command to fire the laser 102; collect the spectra emitted from the plasma 122; input the spectra into the recognition algorithm; and report the resulting identification.

It should now be understood that embodiments of the methods for forming recognition algorithms for identifying materials with laser-induced breakdown spectroscopy described herein, may be utilized to develop recognition algorithms for automated and rapid in situ analysis of materials. Thus, recognition algorithms may be incorporated with a portable LIBS instrument for use by personnel without any specific LIBS expertise. For example, a portable LIBS instrument may be utilized to screen baggage at airports for materials such as, for example, contraband, hazardous chemicals or explosives.

In order that the embodiments described herein may be more readily understood, reference is made to the following example which is intended to illustrate an embodiment of the present disclosure, but not limit to the scope of the disclosure.

EXAMPLE

Spectral data was obtained with a LIBS instrument from thirteen different pathogen species and strains. A recognition algorithm based on chemometric modeling, developed according to the embodiments described herein, was utilized and deployed with a LIBS instrument control system to differentiate bacterial pathogen smears on the surface of a blood agar plate. The recognition algorithm identified five common bacterial pathogens (*Acinetobacter baumanniii, Escherichia coli, Klebsiella pneumoniae, Pseudomonas aeruginosa* and *Staphylococcus aureus*) and the model Gram-positive organism *Bacillus subtilis*. In addition, eight well-characterized clinical and laboratory *S. aureus* strains were identified.

To prepare for LIBS analysis, the bacterial species or strains were streaked onto a fresh Luria broth agar (LBA) plate which was allowed to grow overnight (37° C., 18 hr). Single colonies on the LBA plate were streaked onto a 5% (vol/vol) bovine blood agar (BA) plate and allowed to incubate overnight. The next morning, to create a larger surface area of bacterial material for LIBS data collection, the colonies on the BA plates were spread over the entire surface of the blood agar plate using an ethanol-flamed glass hockey stick.

LIBS spectra were then collected from the blood agar plates using a LIBS instrument (e.g., as depicted in FIG. 2). Specifically, plasma light was collected using an off-axis parabolic mirror and fiber optic and then routed to a dual channel spectrometer (Avantes AvaSpec-ULS2048-2-USB2). It should be noted that the lens-to-sample distance changed during interrogation because the samples were manually moved around in front of the laser beam to target the pathogen on the surface of the blood agar. A hole in the parabolic mirror permitted the optical path of the laser pulses and light collection to be collinear, eliminating parallax. Each recorded spectrum represented the accumulation of ten spectra. A total of 1300 individual spectra (one hundred spectra for each sample) were collected.

The recognition algorithm based on chemometric modeling of the LIBS spectral data was used to successfully differentiate the species and strains. Performance of a LIBS analysis control system on which the algorithm was deployed indicated that two minutes sampling and analysis time was sufficient to determine if a new sample matched one of the thirteen different species and strains studied.

It is noted that the terms "substantially" and "about" may be utilized herein to represent the inherent degree of uncertainty that may be attributed to any quantitative comparison, value, measurement, or other representation. The terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method for forming a recognition algorithm for laser-induced breakdown spectroscopy, the method comprising:

determining a most mathematically different dataset of a plurality of spectral datasets corresponding to materials wherein, the most mathematically different dataset comprises first spectra indicative of light emitted from a first vaporized material;

dividing the spectral datasets into model development datasets and performance evaluation datasets, wherein the model development datasets and the performance evaluation datasets comprise the first spectra;

transforming, automatically with a processor, one of the model development datasets into a first discrimination model that discriminates the first spectra;

removing the first spectra from the model development datasets to yield a subset of development datasets;

determining a next most mathematically different spectral dataset of the spectral datasets, the next most mathematically different spectral dataset comprising second spectra indicative of light emitted from a second vaporized material;

transforming the subset of development datasets into a second discrimination model that discriminates the second spectra; and combining the first discrimination model and the second discrimination model to form the recognition algorithm for laser-induced breakdown spectroscopy.

2. The method of claim 1 further comprising collecting the spectral datasets with a laser-induced breakdown spectroscopy instrument.

3. The method of claim 1 further comprising removing abnormal data from the spectral datasets.

4. The method of claim 1 further comprising normalizing each of the model development datasets.

5. The method of claim 1 further comprising building an overall discrimination model, wherein the most mathematically different dataset is determined with the overall discrimination model.

6. The method of claim 1 further comprising ordering the first discrimination model and the second discrimination model according to discrimination capability, wherein the first discrimination model and the second discrimination model are ordered from highest discrimination capability to lowest discrimination capability and the recognition algorithm invokes the first discrimination model and the second discrimination model in order.

7. The method of claim 1, wherein the model development datasets and the performance evaluation datasets each comprise substantially balanced intensity measurements.

8. The method of claim 1, wherein the model development datasets and the performance evaluation datasets each comprise similar maximum intensity measurements.

9. The method of claim 1, wherein the model development datasets comprise highest intensity measurements of the spectral datasets and the performance evaluation datasets comprise lowest intensity measurements of the spectral datasets.

10. The method of claim 1 further comprising:
    transforming the performance evaluation datasets into screening parameters with the recognition algorithm, wherein the screening parameters are statistics; and
    modifying the recognition algorithm according to the screening parameters.

11. The method of claim 10, wherein the first discrimination model utilizes principal component analysis, partial least squares analysis, multiple regression analysis, or neural network analysis.

12. A method for forming a recognition algorithm for laser-induced breakdown spectroscopy, the method comprising:
    collecting spectral datasets corresponding to materials with a laser-induced breakdown spectroscopy instrument wherein, each of the spectral datasets comprises spectra indicative of light emitted from one of the materials;
    dividing the spectral datasets into model development datasets and performance evaluation datasets;
    transforming, automatically with a processor, the model development datasets into an overall discrimination model, wherein the overall discrimination model identifies each of the materials;
    ranking the spectral datasets from most mathematically different to least mathematically different according to the overall discrimination model;
    creating an individual discrimination model to discriminate a most mathematically different spectral dataset; and
    forming the recognition algorithm for laser-induced breakdown spectroscopy, wherein the recognition algorithm comprises the individual discrimination model.

13. The method of claim 12 further comprising removing the most mathematically different spectral dataset from the model development datasets to yield a subset of development datasets.

14. The method of claim 13 further comprising:
    (a) transforming a next spectral dataset into a next model that discriminates the next spectral dataset;
    (b) removing the next spectral dataset from the subset of development datasets; and
    (c) repeating (a) and (b) if the subset of development datasets comprises more than one of the spectral datasets.

15. The method of claim 14 further comprising adding the next model to the recognition algorithm, wherein models of the recognition algorithm are ordered from most mathematically different to least mathematically different according the spectral datasets corresponding to the models and the recognition algorithm invokes the models in order.

16. The method of claim 14, wherein the spectral datasets of the subset of development datasets are transformed into the next model in order from highest discrimination capability to lowest discrimination capability.

17. The method of claim 12 further comprising transforming the performance evaluation datasets into screening parameters with the recognition algorithm.

18. The method of claim 17 further comprising modifying the recognition algorithm according to the screening parameters.

19. The method of claim 12 further comprising incorporating the recognition algorithm into the laser-induced breakdown spectroscopy instrument.

* * * * *